United States Patent
Goebel et al.

(10) Patent No.: US 11,090,133 B2
(45) Date of Patent: Aug. 17, 2021

(54) DEVICE FOR SIMULTANEOUS FIXATION OF MEDICAL INSTRUMENTS AND CORRESPONDING SYSTEM

(71) Applicant: KARL STORZ SE & Co. KG, Tuttlingen (DE)

(72) Inventors: Werner Goebel, Tuttlingen (DE); Florian Huber, Tuttlingen (DE); Bernhard Gloeggler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 375 days.

(21) Appl. No.: 16/278,996

(22) Filed: Feb. 19, 2019

(65) Prior Publication Data

US 2019/0254773 A1    Aug. 22, 2019

(30) Foreign Application Priority Data

Feb. 22, 2018    (DE) .................... 10 2018 103 968.9

(51) Int. Cl.
*A61B 90/57* (2016.01)
*A61B 17/00* (2006.01)
(Continued)

(52) U.S. Cl.
CPC ........ *A61B 90/57* (2016.02); *A61B 17/00234* (2013.01); *A61B 17/3423* (2013.01);
(Continued)

(58) Field of Classification Search
CPC ......... A61B 90/57; A61B 90/10; A61B 90/50; A61B 17/3462; A61B 2017/348;
(Continued)

(56) References Cited

U.S. PATENT DOCUMENTS 10,639,067 B2 *  5/2020  Tak .................... A61B 17/3415
2004/0243146 A1  12/2004  Chesbrough et al.
(Continued)

FOREIGN PATENT DOCUMENTS

FR           2709942      3/1995
WO    WO 2016/144180    9/2016

OTHER PUBLICATIONS

European Search Report for corresponding European Patent Application No. 19158684.1, dated May 10, 2019.

*Primary Examiner* — Tan-Uyen T Ho
*Assistant Examiner* — Bridget E. Rabaglia
(74) *Attorney, Agent, or Firm* — Jason H. Vick; Sheridan Ross, PC

(57) ABSTRACT

Device for the simultaneous fixation of medical instruments, the device having a joint member which has a holding section in the form of a spherical segment, the spherical segment having a continuous cavity along a longitudinal axis, the holding section being subdivided into at least two holding segments perpendicular to the longitudinal axis, and at least two arm elements being arranged on the joint member, the apparatus further comprising a tension ring supported by the support surfaces and a tensioning element configured to press the support segments together, wherein when the support segments are pressed together, the support surfaces press against the tension ring. Furthermore, a system with such a device is revealed.

21 Claims, 14 Drawing Sheets

(51) Int. Cl.
*A61B 17/34* (2006.01)
*A61B 90/10* (2016.01)
*A61B 90/50* (2016.01)

(52) U.S. Cl.
CPC .......... *A61B 17/3462* (2013.01); *A61B 90/10* (2016.02); *A61B 90/50* (2016.02); *A61B 2017/0042* (2013.01); *A61B 2017/00477* (2013.01); *A61B 2017/347* (2013.01); *A61B 2017/348* (2013.01); *A61B 2017/3492* (2013.01)

(58) Field of Classification Search
CPC .... A61B 2017/0042; A61B 2017/3405; A61B 2017/3407; A61B 90/11; A61B 2017/3403; A61B 2017/3411; A61B 17/34; A61B 17/3415; A61B 17/3468; A61B 17/3403; A61B 2017/347
See application file for complete search history.

(56) References Cited

U.S. PATENT DOCUMENTS

| | | |
|---|---|---|
| 2008/0183191 A1 | 7/2008 | Schoepp |
| 2010/0042111 A1 | 2/2010 | Qureshi et al. |
| 2011/0118545 A1 | 5/2011 | Williams et al. |
| 2012/0296281 A1 | 11/2012 | Jaspers et al. |
| 2016/0007979 A1 | 1/2016 | Bhagat et al. |

* cited by examiner

DEVICE FOR SIMULTANEOUS FIXATION OF MEDICAL INSTRUMENTS AND CORRESPONDING SYSTEM

CROSS REFERENCES TO RELATED APPLICATIONS

This application claims priority from German patent application DE 10 2018 103 968.9, filed on Feb. 22, 2018. The entire contents of this priority application are incorporated herein by reference.

BACKGROUND

This disclosure relates to a device for simultaneous fixation of medical instruments and a system incorporating such a device.

In clinical routine, medical instruments are still positioned by hand or with special support arm systems. The positioning of an instrument inserted in a trocar is of particular interest. Reference is made to the publication US 2012/0296281 A1 as an example.

The requirements for positioning may include, on the one hand, a possibility of a quick positioning in axial direction, i.e. along a longitudinal axis, in particular the endoscope axis. Furthermore, a possibility of rotation around a puncture point, in particular a trocar puncture, is often desired. The pivot point is preferably selected in the immediate vicinity of the puncture point in order to avoid mechanical stress, in particular strain, at the puncture point in the event of a displacement.

WO 2016/144180 A1 shows a tailor-made trocar with a compressible ball joint. The ball-and-socket joint is equipped with a sleeve belt which compresses a ball of the ball-and-socket joint when the belt is tightened and thus fixes an instrument inserted into the trocar. However, it is still desired that the device used for holding the trocar is more flexible with regard to different instruments, especially with regard to the diameter of the instruments.

SUMMARY

One of the objects is to provide a device for the simultaneous fixation of medical instruments, which allows instruments of different diameters to be held and operated with one hand. Furthermore, a corresponding system with two medical instruments is provided.

According to a first aspect, there is provided a device for simultaneously fixing medical instruments, the device comprising a joint member having a holding section in the form of a spherical segment, the spherical segment having a center and a height and defining a longitudinal axis of the device, which runs through the center and parallel to the height, the spherical segment having a continuous cavity along the longitudinal axis, the holding section being subdivided into at least two holding segments, and at least two arm elements being arranged on the hinge part, which each, in a first arm section starting from a fastening point on the hinge part, move away from the longitudinal axis, and, in a second arm section, approach the longitudinal axis and end with a bearing surface, whereby a clearance is formed between the arm elements, the apparatus further comprising a tensioning element configured to compress the holding segments, wherein upon compression of the holding segments, the bearing surfaces move towards the longitudinal axis.

The subdivision into holding segments takes place in such a way that the segmentation can be seen when viewed in a plane perpendicular to the longitudinal axis. This means that a parting plane between two holding segments is not perpendicular to the longitudinal axis. In exemplary embodiments, the parting plane is at an angle to the longitudinal axis of less than 45°, or less than 30°, or less than 15° or less than 5°. The parting plane between two support segments, for some exemplary embodiments, is a flat surface extending outwards from the longitudinal axis. Mathematically formulated, the parting plane then contains the direction vector of the longitudinal axis.

A feature of the device is that an instrument can be guided through the holding section and the holding section is configured to guide the instrument in interaction with the tensioning element. In some exemplary embodiments the force applied by the tensioning element can be adjusted to determine how closely or tightly the instrument is to be guided. In some exemplary embodiments the parting plane is configured in such a way that there is a defined distance between two holding segments if they are arranged concentrically to each other. The distance between the holding segments ensures the functionality of the clamping mechanism. The parting plane can then also be understood as a parting volume, i.e. like a plane with a thickness.

Another feature of the device is that the force exerted on the holding section by the tensioning element is transmitted to the bearing surfaces via the arm elements and an instrument located between the bearing surfaces is clamped. Conversely, by releasing the tensioning element, a pressure exerted by the bearing surface can be reduced or released and thus the clamping of the instrument can be reduced or released. Since the instruments are held and/or fixed in different positions, which also allow different instrument diameters to be taken into account, different instrument combinations can be used without sacrificing ease of use.

Regardless of the number of holding elements and arm elements, in some exemplary embodiments each holding element describes at least substantially the same angle around the longitudinal axis in relation to the longitudinal axis in order to make the individual elements interchangeable. In some exemplary embodiments the sum of the angles of all holding segments is substantially 360°. In some exemplary embodiments, if four holding segments are used, each holding segment may describe an angle of approximately 90° around the longitudinal axis. In some exemplary embodiments, if three holding segments are used, each holding element may describe an angle of approximately 120° around the longitudinal axis. This exemplary embodiment may allow for a good control of the joint member by gripping one of the arm elements. In some exemplary embodiments, if two support segments are used, each support element may describe an angle of approximately 180° around the longitudinal axis.

In some exemplary embodiments the holder is independent of or indifferent regarding the trocar that is used. Furthermore, medical instruments of different types may be fixed or held.

In an exemplary embodiment, the hinge part comprises a flange extending from the holding section along the longitudinal axis and forming a continuation of the cavity, the flange being divided into at least two flange segments, each of which is connected, for some exemplary embodiments, to exactly one holding segment.

The flange may offer a possibility for fastening the arm elements. Since the flange keeps the actual surface of the spherical segment free, the holding section may be moved more freely. The flange can also ensure that a first instrument held by the holding section, especially a trocar, is at least loosely held along the longitudinal axis. Furthermore, the flange can help to ensure that a lateral pressure load on the medical instruments, especially the first instrument, leads to as little displacement as possible away from the longitudinal axis. A contact surface between the joint member and the first instrument can also be selected over the length of the flange, so that pressure on the holding section, and thus on the flange, may allow for to rapid fixation in the case of a large contact surface and may allow for a finely adjustable fixation in the case of a small surface. In some exemplary embodiments, the flange or flange segments are configured in one piece with the holding section or holding segments. In other exemplary embodiments, the flange or holding segments are detachably arranged on the holding section or holding segments. This can be done, for example, by means of a screw or plug connection. An existing flange can then be exchanged for a flange with other dimensions, e.g., for some exemplary embodiments, a different diameter. The number of flange segments does not have to match the number of holding segments. For example, depending on the application, it may be sufficient if there are only two flange segments for three holding segments or if there are two or three flange segments for four holding segments. In principle, there can also be more flange segments than holding segments, which are, for example, plugged together. According to current estimates, however, this may make handling more difficult. Since the flange forms a continuation of the cavity, the first instrument can still be guided through the entire joint member, i.e. both through the holding section and through the flange. For the segmentation of the flange, the same considerations apply as for the segmentation of the joint member. For some exemplary embodiments, the segmentation of the flange is the same as the segmentation of the joint member.

In another exemplary embodiment, the spherical segment has a diameter and the ratio of height to diameter is between 0.35 and 0.99, or between 0.47 and 0.93, or between 0.58 and 0.87, or between 0.7 and 0.8.

This exemplary embodiment is based on the consideration that with a flat spherical segment, i.e. the ratio of height to diameter is rather small, a large cavity can be created in the joint member so that instruments with a large diameter can be fixed relative to the diameter of the joint member. With a flat spherical segment, however, the pivot range of the joint member relative to the tensioning element is rather small. If the spherical segment is chosen very high, i.e. the ratio of height to diameter is rather large and the holding section approaches at least substantially a spherical shape. For some exemplary embodiments, a large pivot range results. In this case, however, the available diameter of the cavity in the joint member becomes relatively small compared to the total diameter of the joint member, so that only a relatively narrow first instrument can be guided through the joint member.

In a further exemplary embodiment, the device further comprises a tensioning ring held by the bearing surfaces, the bearing surfaces pressing against the tensioning ring when the holding segments are pressed together.

This configuration provides an additional option for controlling the clamping of the medical instrument.

In another exemplary embodiment the arm elements can be pivoted on the tensioning ring.

On the one hand, this exemplary embodiment may offer simplified handling and support in that the holding segments can be moved along the longitudinal axis towards and away from the longitudinal axis. Since the arm elements are arranged on the tensioning ring so that they can be pivoted, they may be easy to assemble to form the holding section of the joint member. On the other hand, there is now a counter bearing when the bearing surfaces of the arm elements press against the tensioning ring. In some exemplary embodiments, the arm elements are also detachably arranged on the tensioning ring. The arm elements can then be detached from the tensioning ring, e.g. for sterilization. If the tensioning ring is made of a flexible material, the arm elements can be attached to the tensioning ring using a snap-on connection.

In another exemplary embodiment the contact surfaces are bent to follow the shape of the tensioning ring.

This exemplary embodiment allows the pressure exerted by the contact surfaces to be distributed over a larger area of the tensioning ring. For some exemplary embodiments, this may result in a more even force distribution along the circumference of the tensioning ring. Preferably, the inner radius, relative to the longitudinal axis, of the contact surfaces corresponds to the outer radius of the tensioning ring in the area where the contact surfaces are in contact.

In another exemplary embodiment, the tensioning ring has a recess for each bearing surface, into which a respective bearing surface can be detachably suspended, so that the respective arm element can be pivoted around the respective bearing surface as a pivot point relative to the longitudinal axis.

This exemplary embodiment may make the device easy to handle. By attaching the arm elements, good pre-positioning of the arm elements and thus of the holding segments can be achieved on the one hand. On the other hand, the arm elements are detachably attached to the tensioning ring so that good autoclavability of the arm elements is guaranteed.

In another exemplary embodiment, two adjacent holding segments mesh with each other via a tongue-and-groove connection.

This exemplary embodiment may allow for the holding segments to assume a defined position relative to each other even if the holding segments do not yet lie against each other on their side surfaces. Furthermore, the tongue-and-groove connection helps to ensure that the holding elements maintain their relative position to each other at least substantially even in the relaxed state of the tensioning element. In some exemplary embodiments, the groove is inserted into one of the two side surfaces of a holding segment and opens into the cavity. In some exemplary embodiments the groove is aligned perpendicular to the longitudinal axis. The side surfaces are those surfaces of a holding segment with which a holding segment adjoins the adjacent holding segment.

In another exemplary embodiment, the holding section has exactly three holding segments and exactly one arm element is arranged on each holding segment.

On the one hand, this exemplary embodiment may allow for a good handling, as three holding segments can be easily assembled. In addition, the division into three holding segments may provide for a good force distribution on a held second instrument. In some exemplary embodiments, if handling is to be improved, exactly two holding segments may be used. If the force distribution and the position of the individual arm elements on the second medical instrument is to be improved, four, five, six or more holding segments are used in some exemplary embodiments. Although the aspect that exactly one arm element is arranged on each holding segment is independent of the exactly three holding segments, for some exemplary embodiments, with regard to the interchangeability of the holding segments, each of the three holding segments has exactly one arm element, so that exactly three arm elements are present.

In another exemplary embodiment, the arm elements are positioned at an angle of at least 45° around the longitudinal axis, or at least 60°, or at least 90°, or at least 120° apart.

This exemplary embodiment may allow for a good access to the longitudinal axis of the device in the area of the arm elements, even if many arm elements are used. Especially if the first instrument is an instrument with one or more connections, the connections of the first instrument are still easily accessible with this configuration. In some exemplary embodiments with three support segments, each arm element is 120° apart from the adjacent arm element.

In another exemplary embodiment, each arm element has a third arm section located between the first arm section and the second arm section which, for some exemplary embodiments, extending at least substantially parallel to the longitudinal axis.

This exemplary embodiment may allow for the use of very different trocar shapes. For some exemplary embodiments the length of the second arm sections, makes it possible to use trocars with large heads. In addition, some exemplary embodiments may allow for a comfortable gripping of the arm element and thus a well controllable shifting of the joint member.

In another exemplary embodiment, the tensioning element has two tensioning levers connected to a hinge, each tensioning lever having a pressure region configured to hold the joint member and to press against the holding section when the tensioning levers are pressed together, the tensioning levers being connected, for some exemplary embodiments, to a tensioning screw configured to press the tensioning levers together.

This exemplary embodiment may offer a good manufacturability and can be reliably sterilized. In some exemplary embodiments, the pressure area is configured as a conical bearing surface, the radius of which corresponds at least substantially to the radius of the spherical segment. In other exemplary embodiments, the pressure area of each tensioning lever is formed by two linear supports, whereby, in some exemplary embodiments, the linear supports run at least substantially parallel to each other. Such an exemplary embodiment can be achieved, for example, by the fact that the radius of the conical bearing surface is smaller than the radius of the spherical segment. The joint member then rests only on the borders of the bearing surface, so that the bearing surface itself can be omitted.

In another exemplary embodiment, the tensioning ring has an annular base element and at least two extensions which can be displaced relative to the base element along the longitudinal axis and the tensioning ring is held on the extensions.

This exemplary embodiment may allow for a good control over the clamping effect of the tensioning ring. The extensions are not directly connected to each other, but are simply arranged together on the base element. The geometric embodiment of the projections can be used to determine to what extent the projections shift to the longitudinal axis as a result of the force exerted by the bearing surfaces. In general, the further the extensions can bend in the direction of the longitudinal axis, the greater the range of possible diameters of the second instrument that can be reliably held by the tensioning ring. If the tensioning ring is subjected to pressure by the contact surfaces via the extensions, the base element may remain essentially dimensionally stable, while the extensions move with their free ends along the longitudinal axis by bending.

In another exemplary embodiment, an elastic holding element is inserted in the holding section, which is configured to hold a first instrument of the medical instruments along the longitudinal axis.

In this configuration, the elastic holding element enables differences in diameter to be compensated between a first inner diameter of the joint member, possibly in connection with a flange, and an outer diameter of the first medical instrument. Depending on the selected thickness of the holding element, the first instruments can also be guided in the joint member, the outer diameter of which is considerably smaller than the inner diameter of the joint member.

In another exemplary embodiment, the holding section is configured to hold a first instrument of the medical instruments and the tensioning ring is configured to hold a second instrument of the medical instruments.

Since the instruments are held in different places, a good individual positioning and fixation may be possible.

In another exemplary embodiment the holding section is configured to guide a trocar and the tensioning ring is configured to hold an endoscope that is inserted into the trocar.

This exemplary embodiment is designed for a typical application. The inner diameter of the joint member may be between 5 and 15 millimeters, or between 7 and 13 millimeters, or between 8 and 12 millimeters. The outer diameter of the endoscope is at least slightly smaller than the inner diameter of the trocar and is, in some exemplary embodiments, smaller than 10 millimeters, especially smaller than 7 millimeters and especially smaller than 5 millimeters.

According to another aspect, there is provided a device as described above, a trocar and an endoscope, the trocar being guided from the holding section along the longitudinal axis and the endoscope being inserted into the trocar and held by the tensioning ring along the longitudinal axis.

It goes without saying that the features mentioned above and those to be explained below can be used not only in the combination indicated, but also in other combinations or in isolation, without leaving the scope of this disclosure.

BRIEF DESCRIPTION OF THE DRAWINGS

Exemplary embodiments of the disclosure are shown in more detail in the drawing and are explained in more detail in the following description.

DESCRIPTION OF EXEMPLARY EMBODIMENTS

Figure 1:
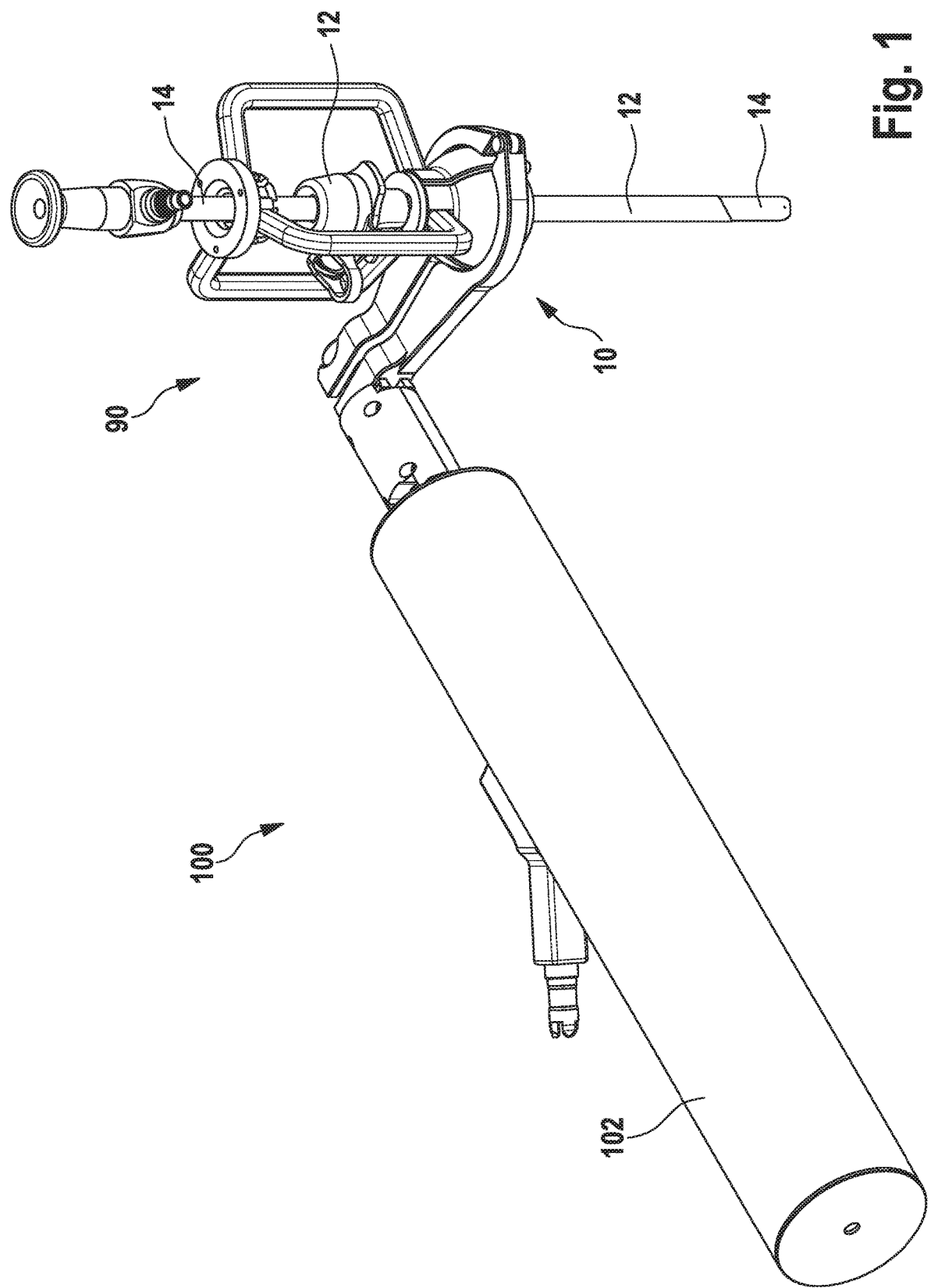
FIG. 1 illustrates a holding device with a system coupled to it.

FIG. 1 shows an apparatus 100 comprising a pulling device 102 to which a device 10 is coupled. The device 10 fixes a first medical instrument 12, here a trocar, and a second medical instrument 14, here an endoscope. The device 10, the first medical instrument 12 and the second medical instrument 14 form a system 104. The device 10 is now explained in more detail below.

Figure 2:
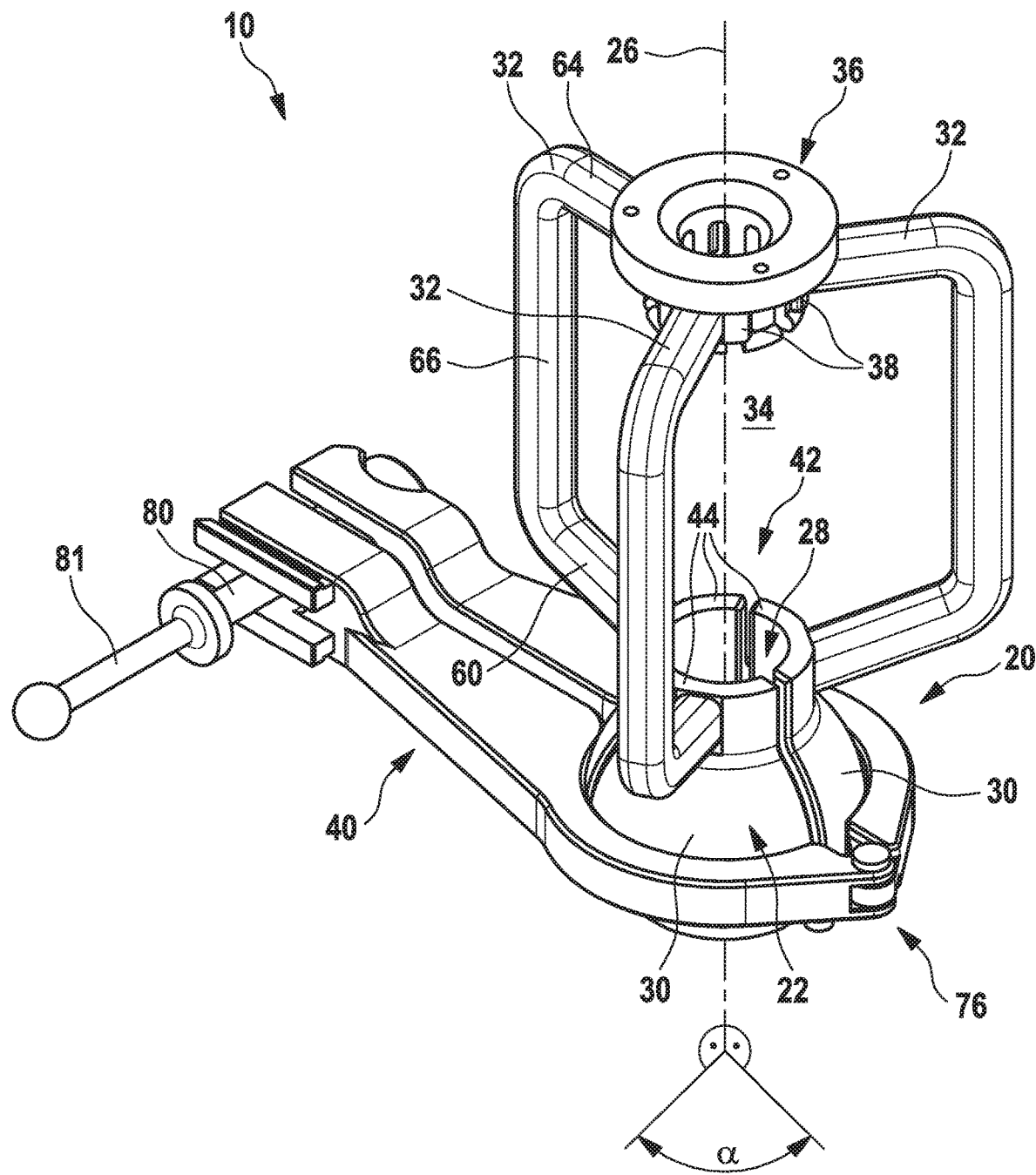
FIG. 2 illustrates an exemplary embodiment of the device.

FIG. 2 shows the device 10 of FIG. 1. The device 10 has a joint member 20 which has a holding section 22 in the form of a spherical segment 24. The shape of the spherical segment 24 will be explained in more detail later on. The course of a longitudinal axis 26 of the device 10 is also explained.

Figure 8:
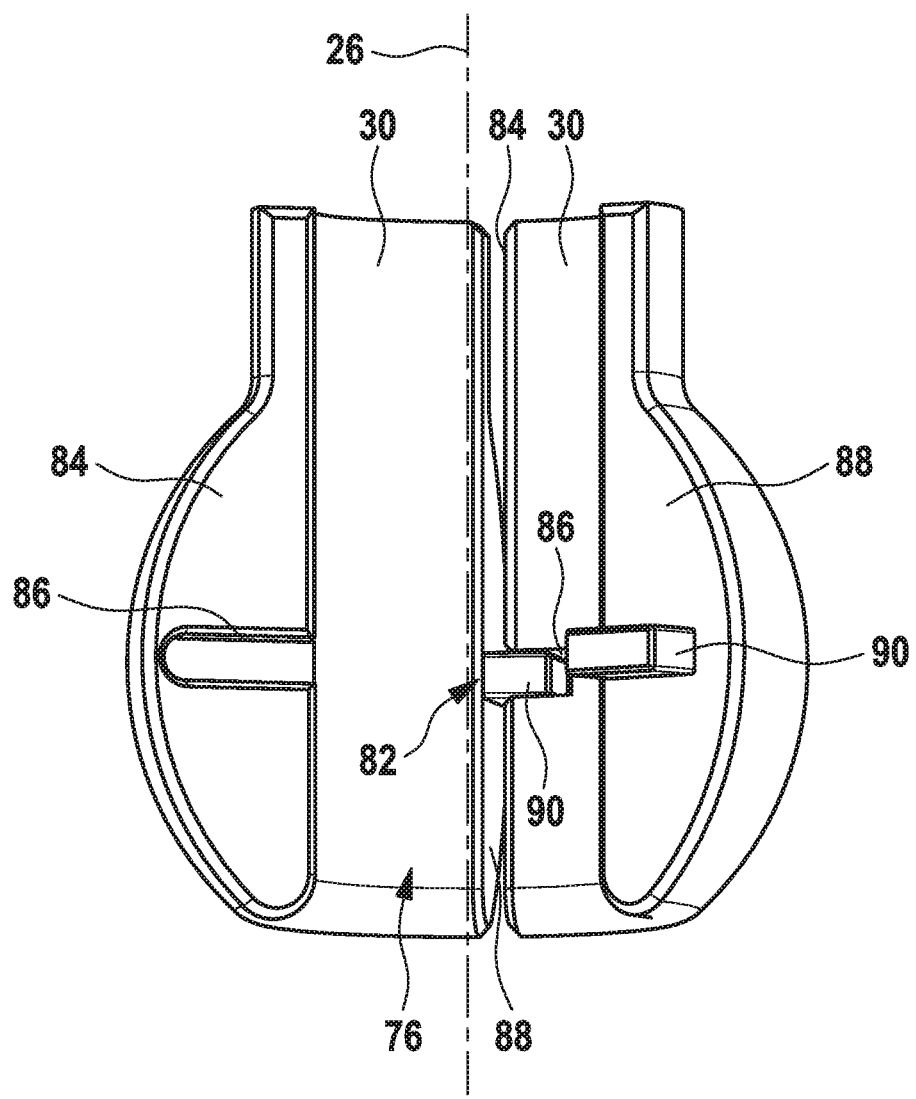
FIG. 8 illustrates an exemplary embodiment of a tongue and groove connection between two holding segments according to the exemplary embodiment of FIG. 2.

The joint member 20 has a continuous cavity 28 along the longitudinal axis 26, see also the opened illustration in FIG. 8. The holding section 22 is divided into at least two holding segments 30 in a plane perpendicular to the longitudinal axis 26, the exemplary embodiment shown here having three holding segments 30.

At least two arm elements 32 are arranged on the joint member 20, whereby the exemplary embodiment shown has three arm elements 32. Due to the shape of the arm elements 32, a clearance 34 is formed between the arm elements 32.

The device 10 also has a tensioning ring 36 which is held by bearing surfaces 38. The device 10 also has a tensioning element 40 which is configured to press the holding segments 30 together, whereby when the holding segments 30 are pressed together, the bearing surfaces 38 press against the tensioning ring 36.

The joint member 20 has a flange 42 which extends from the holding section 22 along the longitudinal axis 26 and forms a continuation of the cavity 28, the flange 42 being divided into at least two flange segments 44 perpendicular to the longitudinal axis 26. In this exemplary embodiment, flange 42 is divided into three flange segments 44. In addition, in this exemplary embodiment each flange segment 44 is connected to exactly one holding segment 30, by providing a single holding segment 30 integral with the corresponding flange segment 44. The arm elements 32 are spaced 120° apart from each other in relation to an angle α around the longitudinal axis 26 and are configured in one piece with the respective flange segment 44.

The holding section 22 is configured to guide the first instrument 12, and the tensioning ring 36 is configured to hold the second instrument 14. Specifically, in this exemplary embodiment, the holding section 22 is configured to hold a trocar and the tensioning ring 36 is configured to hold an endoscope inserted into the trocar.

Figure 3:
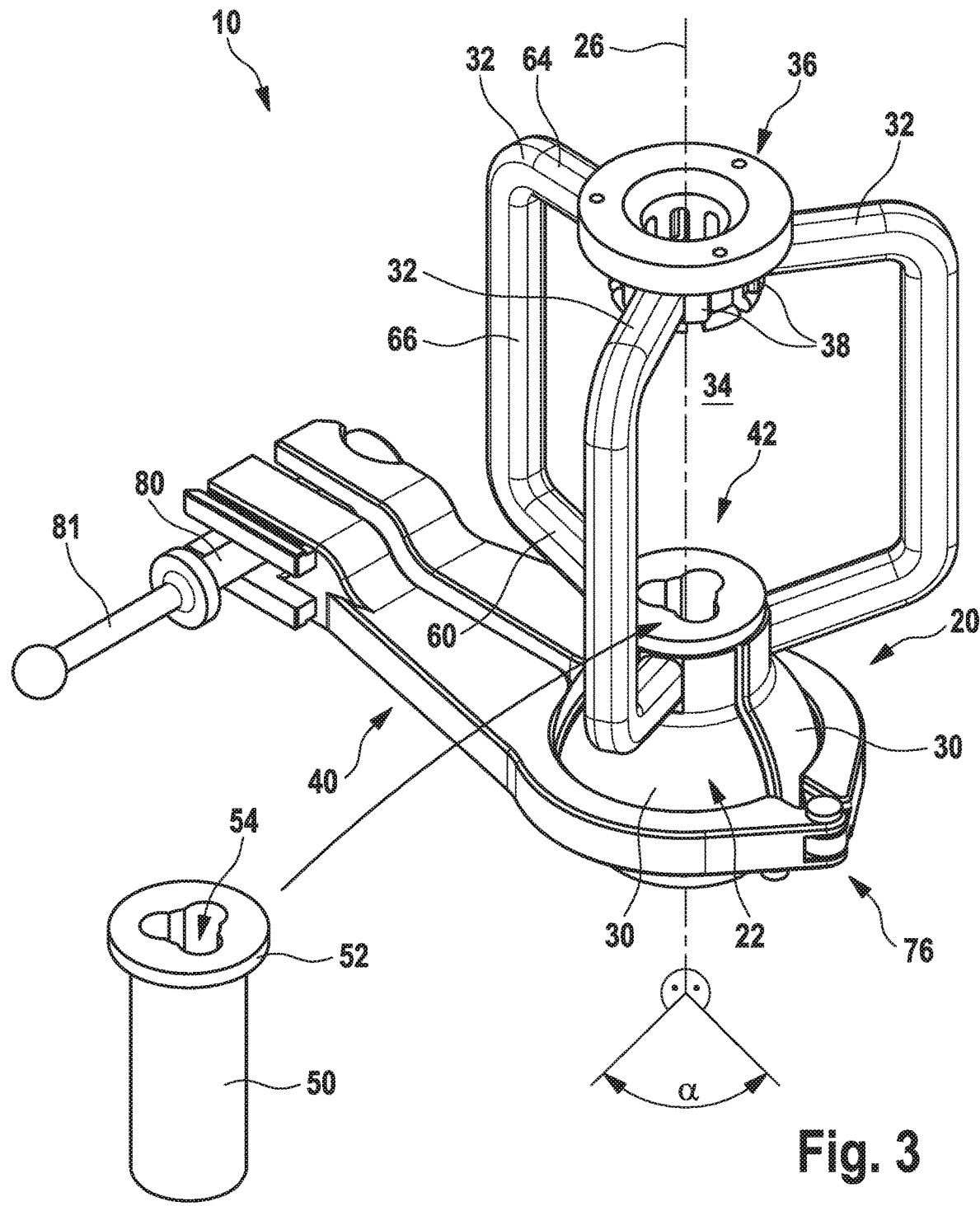
FIG. 3 illustrates the exemplary embodiment according to FIG. 2 with an inserted elastic holding element.

FIG. 3 shows the device 10 shown in FIG. 2, wherein now an elastic holding element 50 is inserted into the holding section 22 which is configured to receive the first instrument 12 along the longitudinal axis 26. To illustrate the shape of the holding element 50, it is shown also outside the fixture 10. It can be seen that the holding element 50 has a substantially cylindrical shape and terminates at its upper end with a bead 52. A recess 54 within the support member 50 is in the form of four composite circles, one center of a large first circle coinciding with the longitudinal axis 26 and three further smaller circles offset from the longitudinal axis 26 and spaced at an angle α of 120° about the longitudinal axis.

Figure 4:
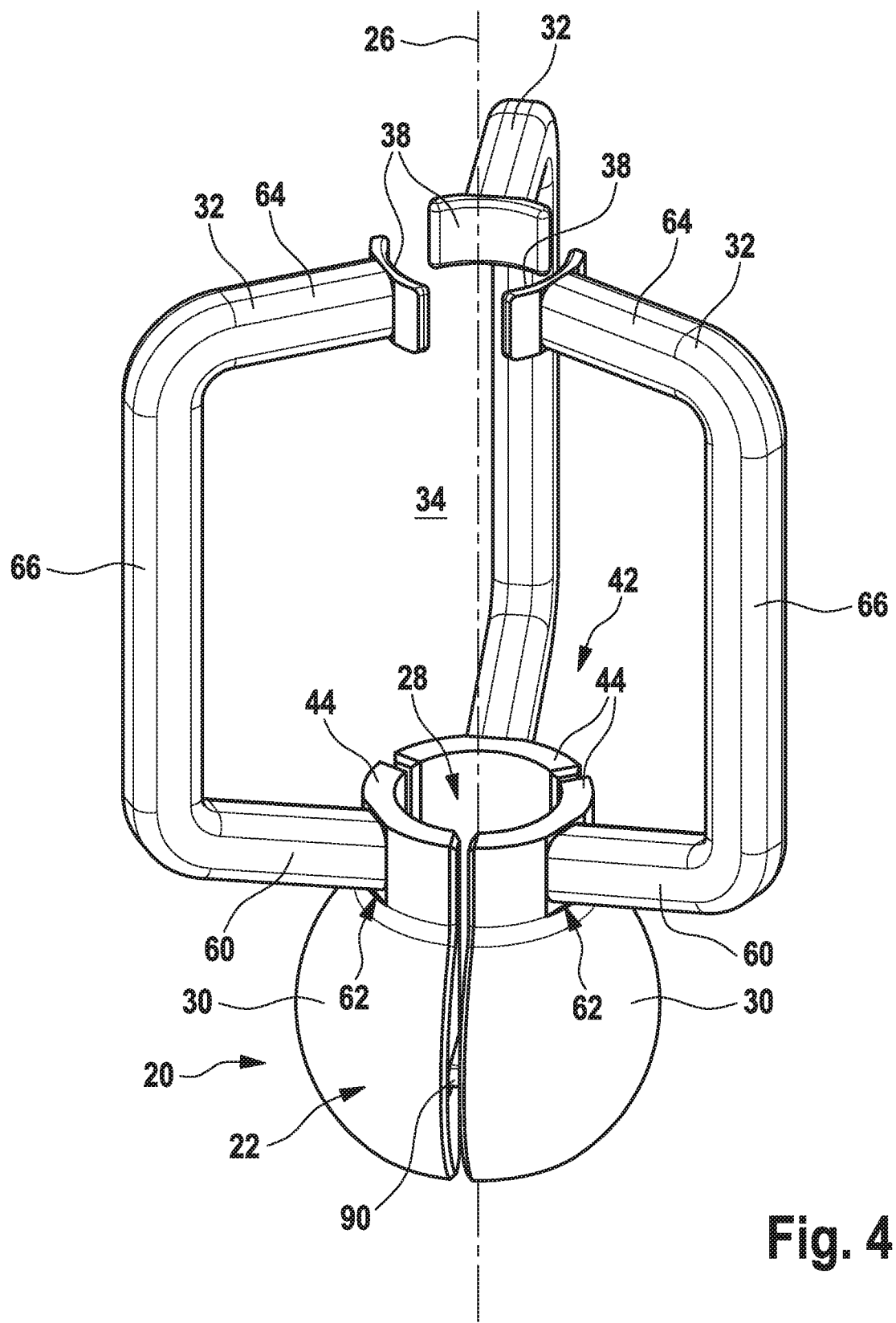
FIG. 4 illustrates the joint member and the three arm elements of the exemplary embodiment according to FIG. 2.

FIG. 4 shows the joint member 20 with three arm elements 32 according to the exemplary embodiment of FIG. 2. It can be seen that the bearing surfaces 38 of the arm elements 32 are bent to follow the shape of the tensioning ring 36, the latter not shown here.

Figure 5:
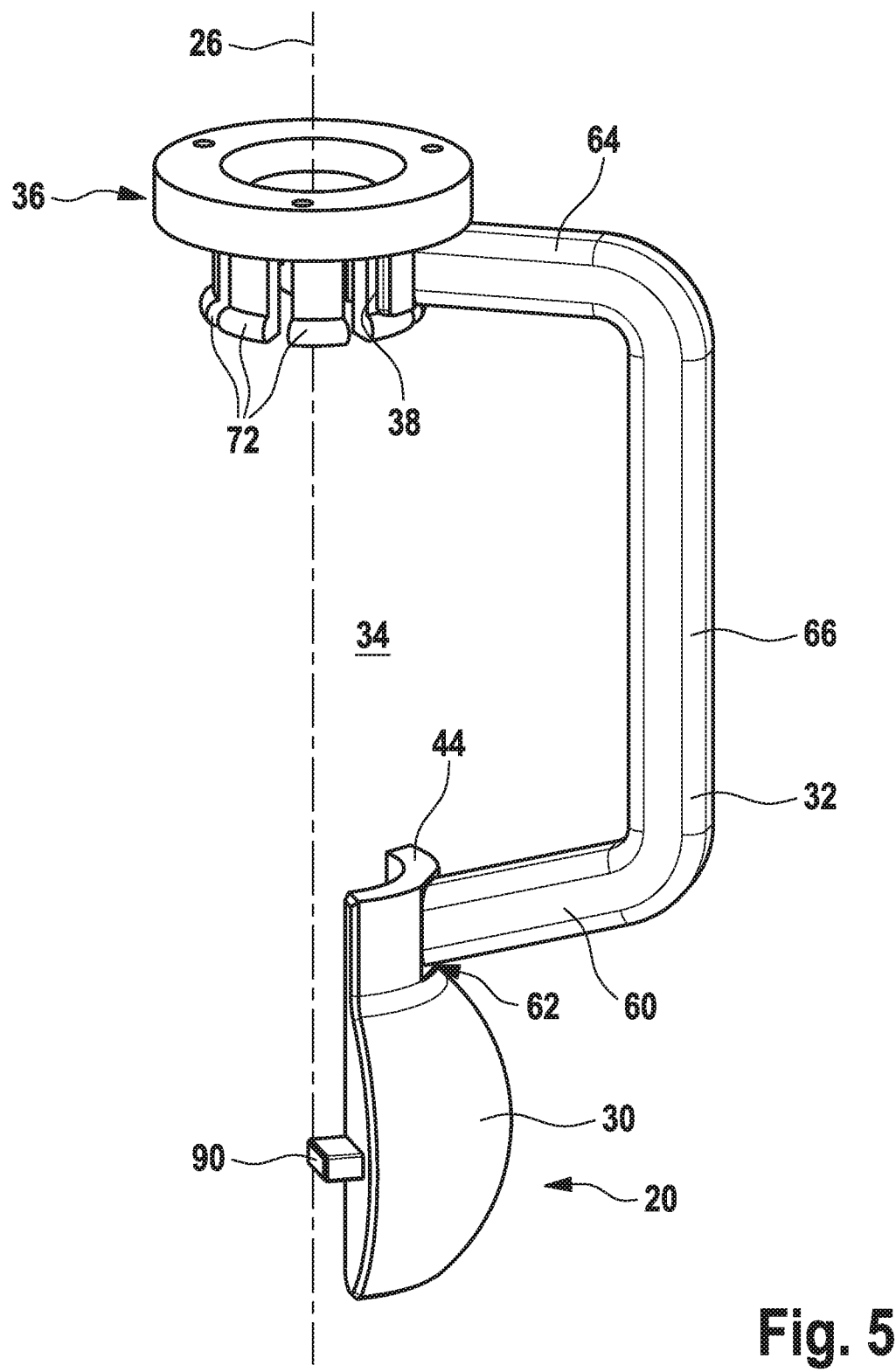
FIG. 5 illustrates a holding segment with the corresponding arm element, which extends to the tensioning ring.

FIG. 5 shows a holding segment 30, an arm element 32 and the tension ring 36. It is shown that the arm element 32, like the other arm elements 32, has a first arm section 60 starting from a fixation point on the joint member 20, which moves away from the longitudinal axis 26. At the other end of the arm element 32 there is a second arm section 64 which approaches the longitudinal axis 26. The second arm section 64 and thus the arm element 32 terminate in the bearing surface 38. The arm element 32 further comprises a third arm section 66 disposed between the first arm section 60 and the second arm section 64. The third arm section 66 may extend, for some exemplary embodiments as shown here, at least substantially parallel to the longitudinal axis 26.

Figure 6:
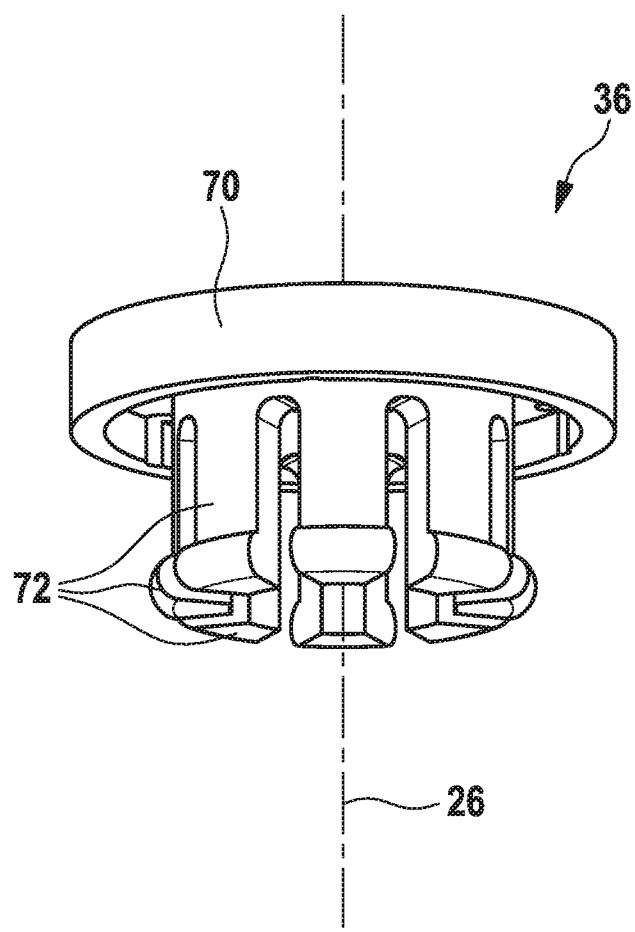
FIG. 6 illustrates another exemplary embodiment of a tensioning ring.

FIG. 6 shows the tensioning ring 36 according to the exemplary embodiment of FIG. 2. The tensioning ring 36 has a ring-shaped base element 70 and at least two extensions 72, whereby eight extensions 72 are shown with this exemplary embodiment. The extensions 72 can be shifted relative to the base element 70 towards the longitudinal axis 26. For this exemplary embodiment, the free ends of the extensions 72 move towards the longitudinal axis 26. The tensioning ring 36 is held by the bearing surfaces 38 on the extensions 72.

Figure 7:
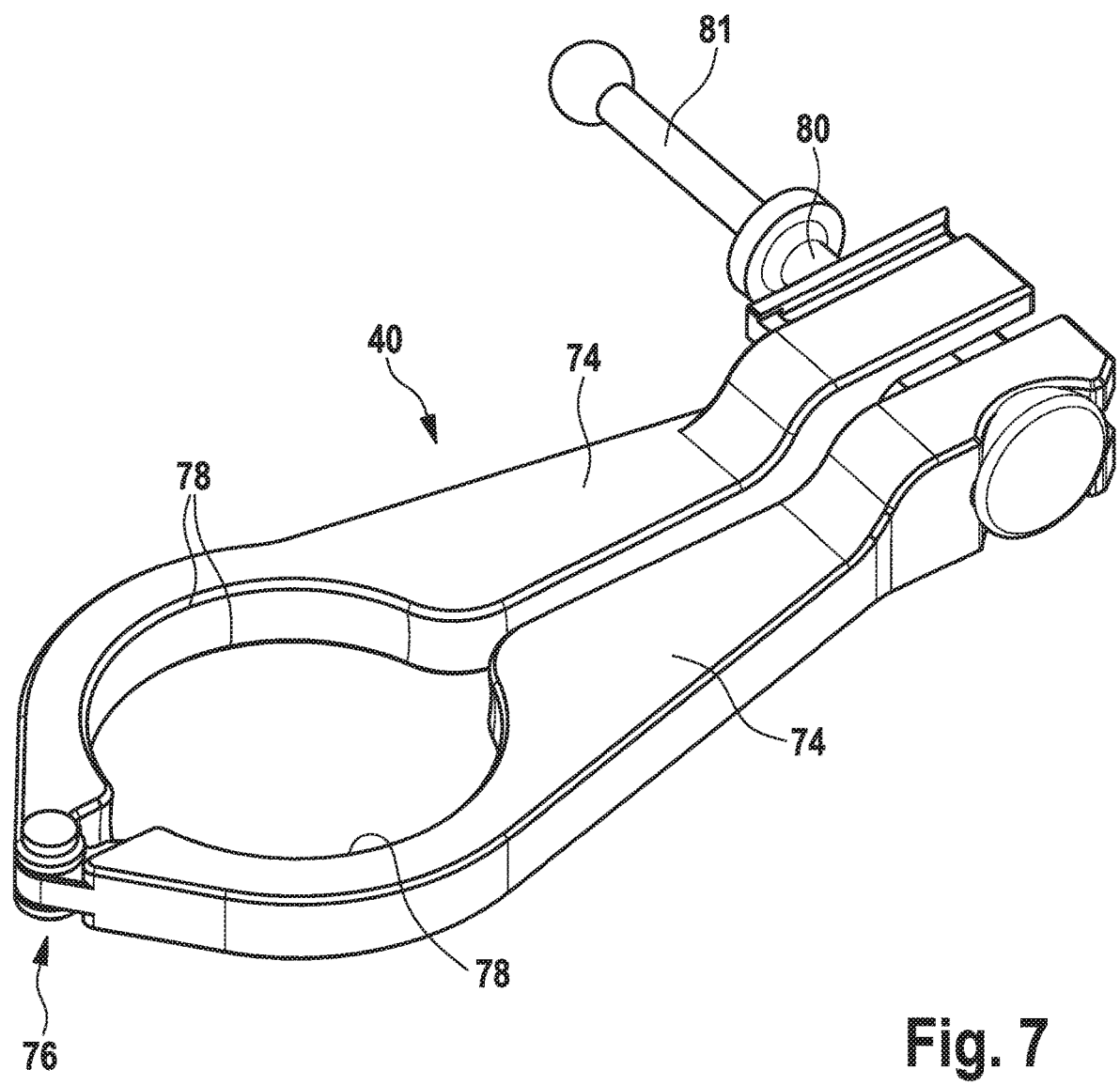
FIG. 7 illustrates the tensioning element according to the exemplary embodiment of FIG. 2.

FIG. 7 shows the tensioning element 40 from the exemplary embodiment of FIG. 2. The tensioning element 40 has two tensioning levers 74 which are connected with a hinge 76. Each tensioning lever 74 has a pressure area 78 which is configured to hold the joint member 20. The pressure area 78 is also configured to press against the holding section 22 when the tensioning levers 74 are pressed together. In this exemplary embodiment, the tensioning levers 74 are connected to a tensioning screw 80, which is configured to press the tensioning levers 74 together. The tensioning screw 80 here has an extension 81 which couples the device 10 to the pulling device 102.

FIG. 8 shows how two adjacent holding segments 30 mesh with each other via a tongue-and-groove connection 82 in the exemplary embodiment of FIG. 2. For this purpose the two holding segments 30 each have a groove 86 on their first side face 84 and a tongue 90 on their second side face 88. The grooves 86 may open into the cavity 28. The grooves 86 may be arranged substantially in the middle of the respective holding segment 30, relative to the longitudinal axis 26, and do not penetrate the outer surface of the respective holding segment 30.

Figure 9:
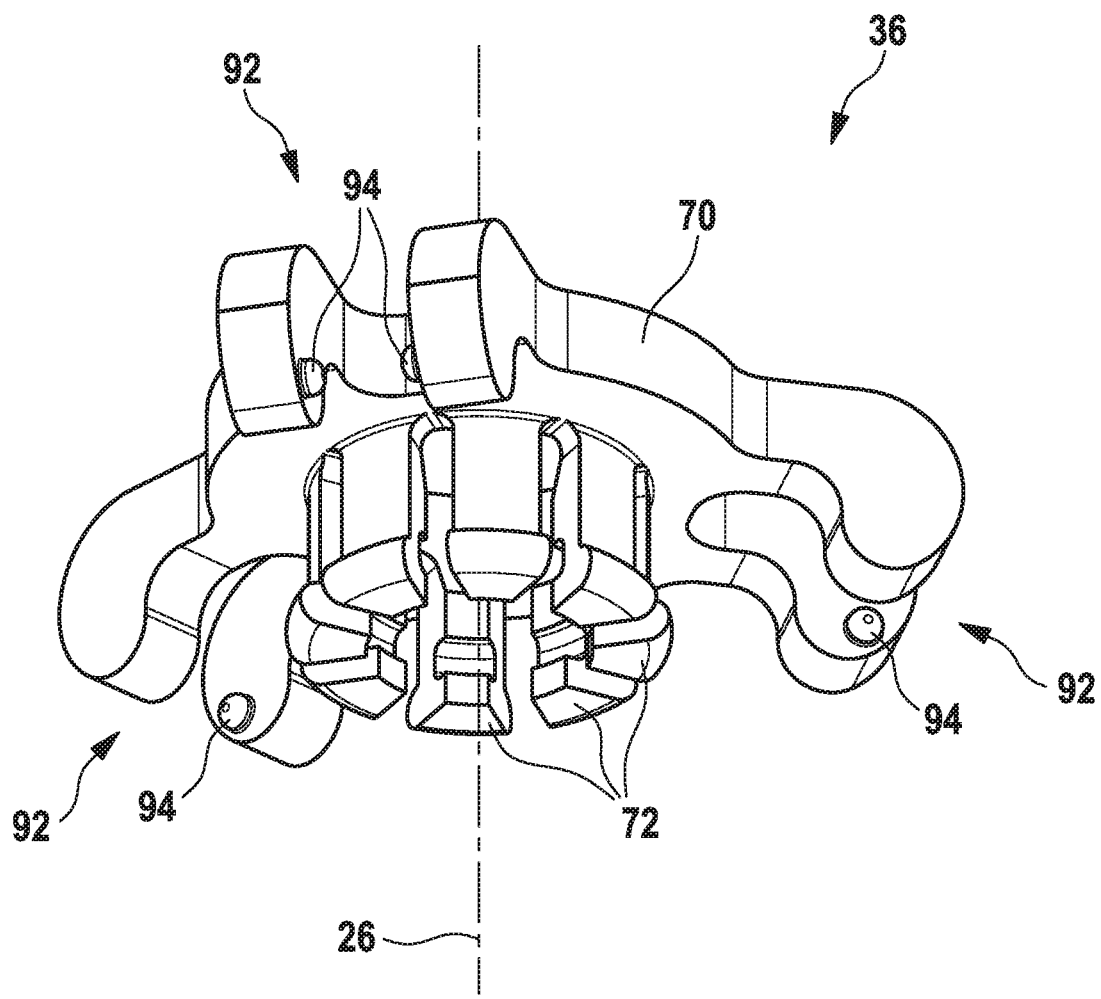
FIG. 9 illustrates a second exemplary embodiment of a tensioning ring.

FIG. 9 shows a third exemplary embodiment of a tensioning ring 36. The tensioning ring 36 has a ring-shaped base element 70 and eight extensions 72. Furthermore, three holders 92 are attached to the tensioning ring 36 starting from the base element 70, which protrude perpendicularly to the longitudinal axis 26. Each of the brackets 92 has two projections 94, into which arm elements 32 with their second arm section 64 can be suspended or clipped.

Figure 10:
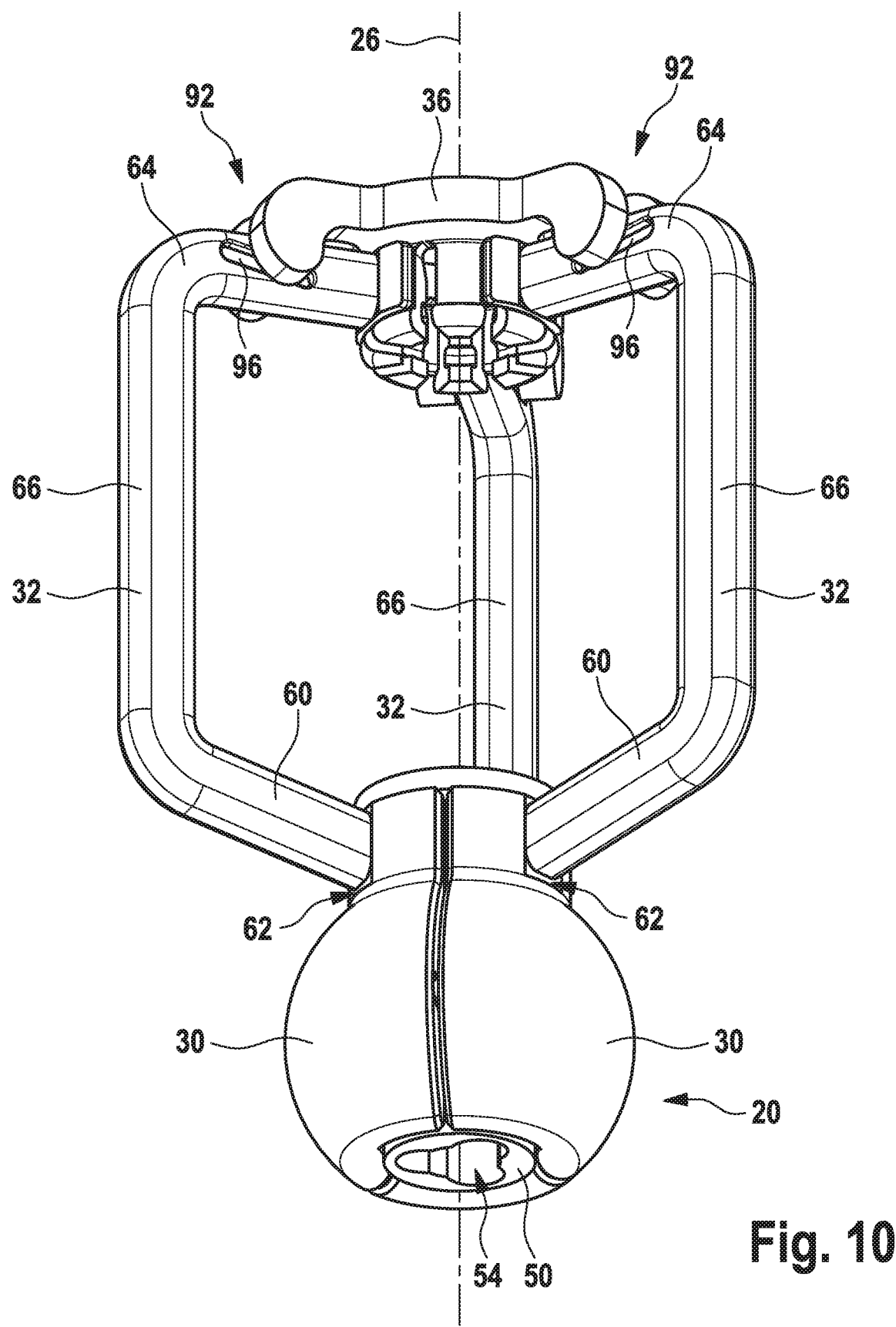
FIG. 10 illustrates the interaction of the tensioning ring of FIG. 9 with a second exemplary embodiment of arm elements.

FIG. 10 shows the tensioning ring 36 of FIG. 9, whereby the arm elements 32 are now shown which are suspended or clipped into the brackets 92. For this purpose 64 grooves 96 are formed on the arm elements 32 in the area of the respective second arm sections. With this exemplary embodiment, the arm elements 32 are thus arranged on the tensioning ring 36 so that they can be pivoted.

Figure 11:
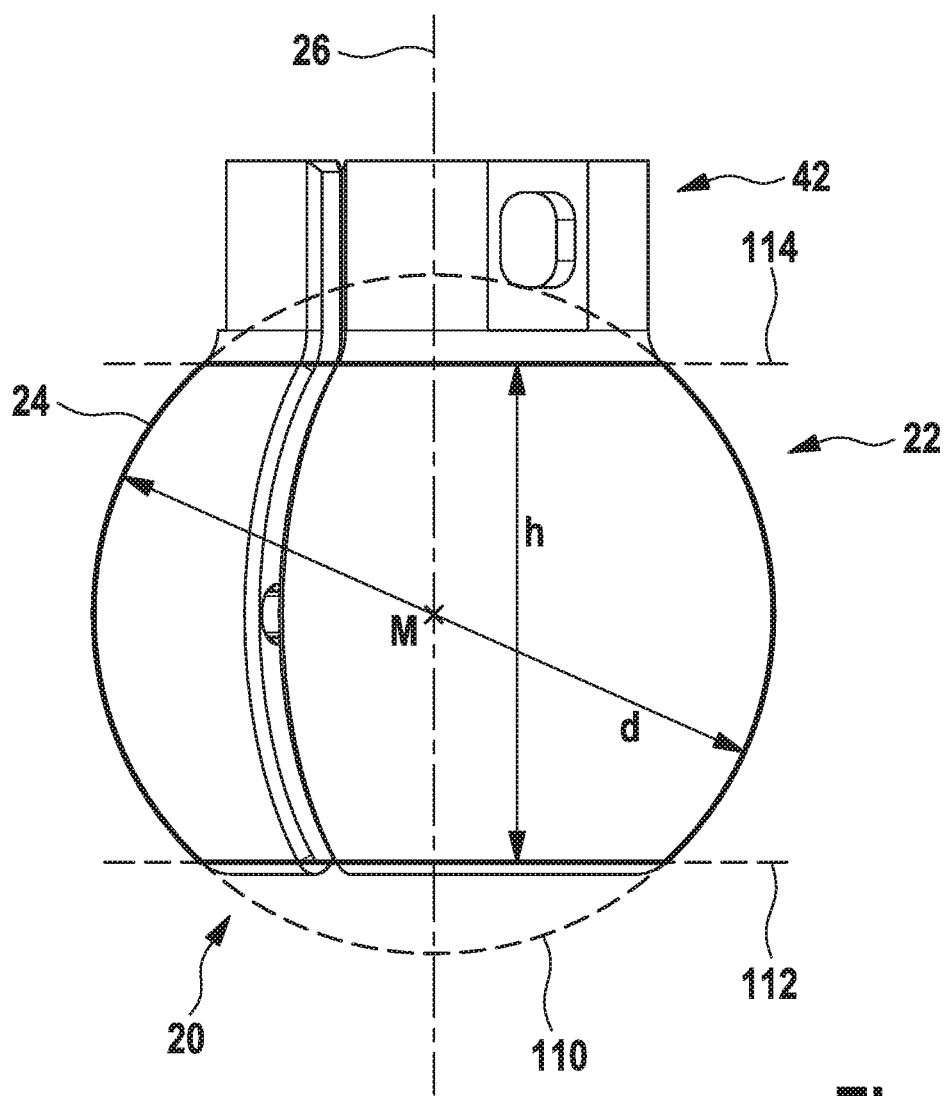
FIG. 11 illustrates a representation of the spherical segment.

FIG. 11 explains the shape of the spherical segment 24, which has the holding section 22. For this purpose the holding section 22 is shown in such a way that the longitudinal axis 26 runs exactly in the drawing plane. The spherical segment 24 is created by cutting the sphere 110 from the planes 112 and 114, which are perpendicular to the longitudinal axis 26. The spherical segment 24 has a center M, a diameter d and a height h. In this exemplary embodiment, the longitudinal axis 26 of the device is defined by the fact that it passes through the center M and is parallel to the height h.

The distance of planes 112 and 114 from the center M along the longitudinal axis 26 is at least substantially equal. However, the distances of planes 112, 114 from the center M can also be different. Planes 112, 114 may also be at an angle α to the longitudinal axis 26, provided that the shape remains at least substantially one of a spherical segment.

Figure 12:
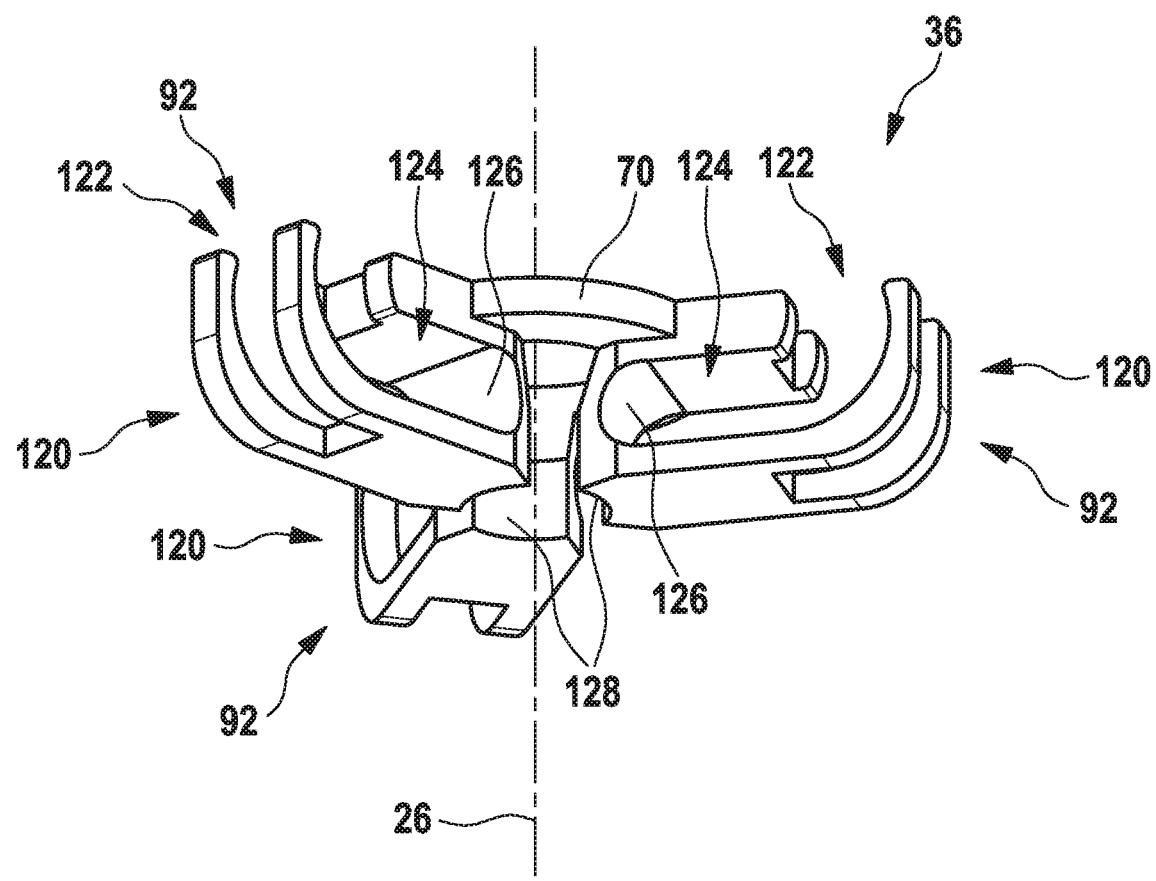
FIG. 12 illustrates a third exemplary embodiment of a tensioning ring.

FIG. 12 shows a third exemplary embodiment of a tensioning ring 36. The tensioning ring 36 has three holders 92, which are configured as recesses 120. Relative to the longitudinal axis 26, the recesses 120 here begin with an outer insertion section 122, which merges into a feed section 124.

The feed section 124 is bounded by a contact surface 126. The contact surface 126 is configured to absorb a pressure from the contact surface 38 of the respective arm 32 so that a corresponding pressure surface 128 located further inside can be pressed in the direction of the longitudinal axis 26, here, for this exemplary embodiment, against the second instrument 14.

Figure 13:
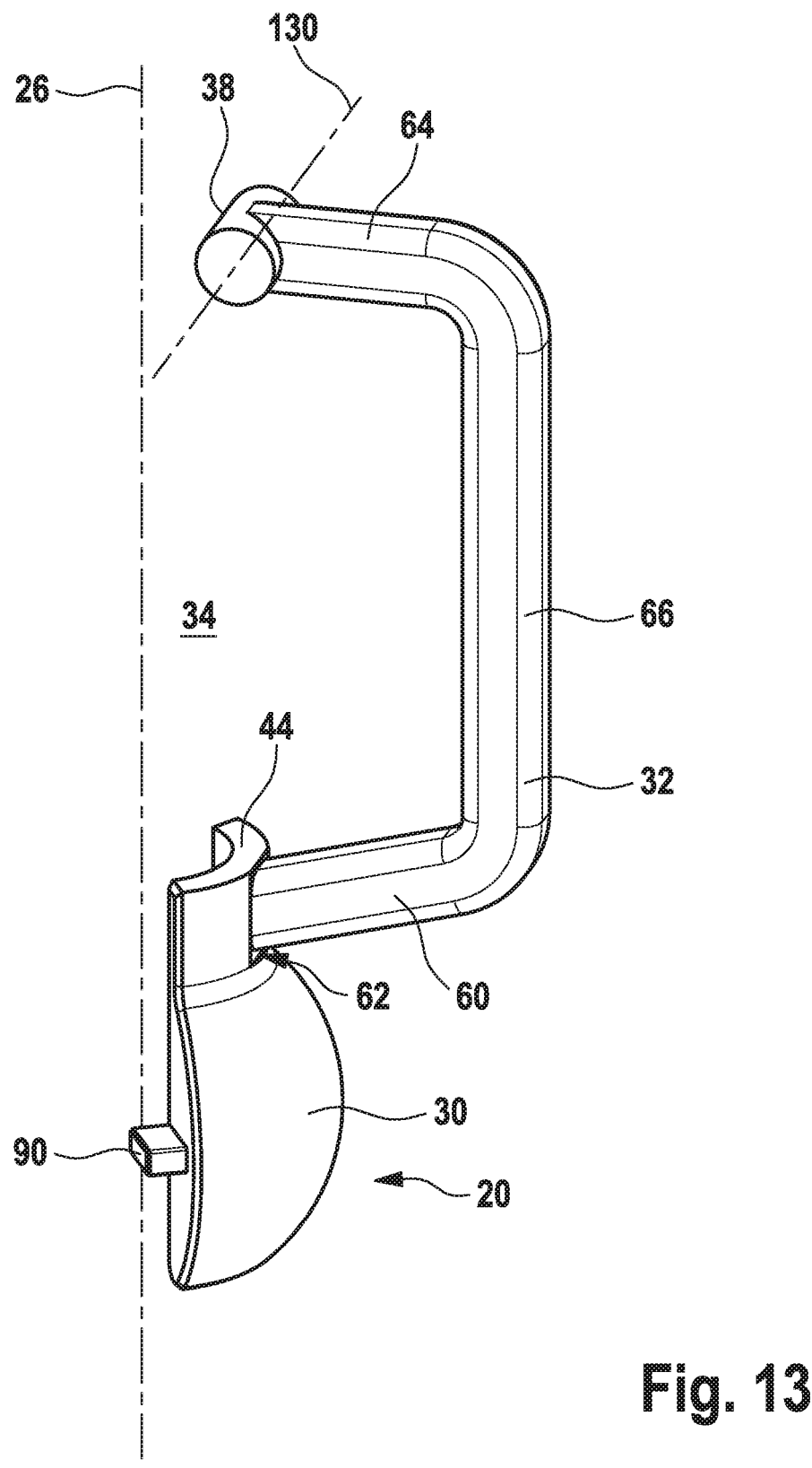
FIG. 13 illustrates a third exemplary embodiment of arm elements with a modified bearing surface.

FIG. 13 shows an arm element 32 according to a third exemplary embodiment. All previous explanations regarding the arm element 32 apply. However, the contact surface 38 here is configured in the form of a cylinder. Other curved surfaces are also conceivable, such as a semi-cylindrical or quarter-cylindrical surface or a spherical or hemispherical surface. In principle, other shapes of the bearing surface 38 can also be selected, for example as shown in FIG. 5, provided that force transmission from the arm element 32 via the bearing surface 38, the bearing surface 126 to the pressure surface 128 is ensured. A rounded surface may allow, for some exemplary embodiments, for an easy pivoting of the arm elements 32 relative to the longitudinal axis 26. In principle, however, the contact surface 38 can also be formed by a cuboid or a prism, for example.

In the exemplary embodiment shown here, the alignment of the cylindrical bearing surface 38 is selected so that the center axis 130 of the cylindrical bearing surface 38 represents the tangent of a circle which is perpendicular to the longitudinal axis 26 and has the longitudinal axis 26 as the center.

Figure 14:
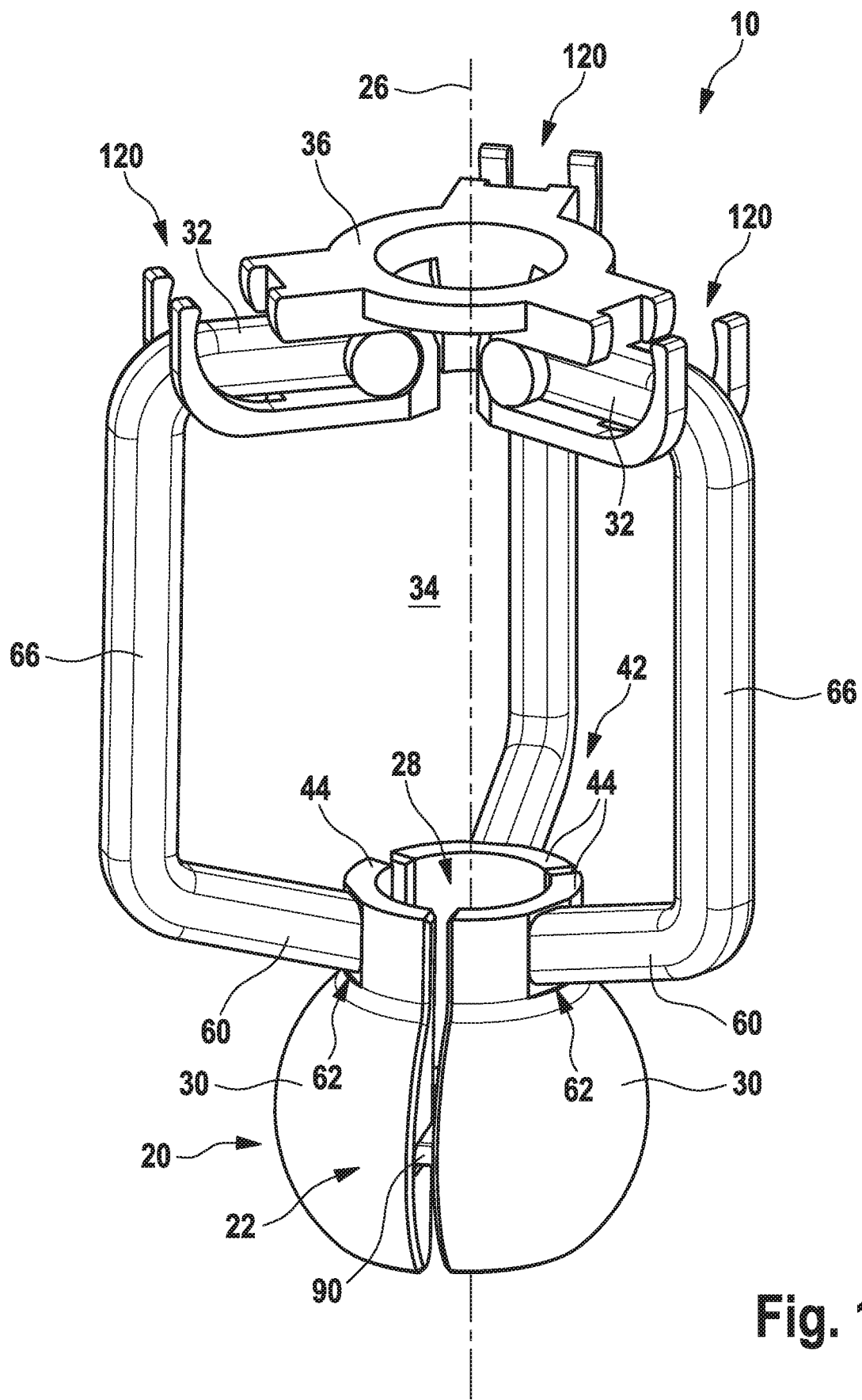
FIG. 14 illustrates the interaction of the tensioning ring of FIG. 12 with the exemplary embodiment of arm elements of FIG. 13.

FIG. 14 shows a third version of the device 10, in which arm elements 32 according to FIG. 13 are hooked into the tension ring 36 according to FIG. 12.

What is claimed is:

1. A device for simultaneously fixing medical instruments, the device comprising a joint member having a holding section in the form of a spherical segment, the spherical segment having a center and a height and defining a longitudinal axis of the device, which runs through the center and parallel to the height, the spherical segment having a continuous cavity along the longitudinal axis, the holding section being subdivided into at least two holding segments, and at least two arm elements being arranged on a hinge part, which each, in a first arm section starting from a fastening point on the hinge part, move away from the longitudinal axis, and, in a second arm section, approach the longitudinal axis and end with a bearing surface, whereby a clearance is formed between the arm elements, the device further comprising a tensioning element configured to press the holding segments together, wherein upon pressing the holding segments together, the bearing surfaces move towards the longitudinal axis.

2. The device of claim 1, wherein the joint member comprises a flange which extends along the longitudinal axis from the holding section and forms an extension of the cavity, wherein the flange is divided into at least two flange segments.

3. The device of claim 1, wherein at least two flange segments are each connected to exactly one holding segment of the at least two holding segments.

4. The device of claim 1, the spherical segment having a diameter and the ratio of the height to the diameter being between 0.35 and 0.99.

5. The device of claim 1, the spherical segment having a diameter and the ratio of the height to the diameter being between 0.58 and 0.87.

6. The device of claim 1, further comprising a tensioning ring which is held by the bearing surfaces, the bearing surfaces pressing against the tensioning ring when the holding segments are pressed together.

7. The device of claim 6, wherein the arm elements are pivotably arranged on the tensioning ring and/or the bearing surfaces are bent in order to follow the shape of the tensioning ring.

8. The device of claim 6, wherein the tensioning ring has for each bearing surface a recess into which a respective bearing surface can be detachably suspended, so that a respective arm element of the at least two arm elements can be pivoted about the respective bearing surface as a pivot point relative to the longitudinal axis.

9. The device of claim 1, wherein two adjacent holding segments are in engagement with one another via a tongue-and-groove connection.

10. The device of claim 1, wherein the at least two holding segments are provided as has exactly three holding segments and on each holding segment of the exactly three holding segments is arranged exactly on one arm element of said at least two arm elements.

11. The device of claim 1, wherein the arm elements are spaced from one another at an angle around the longitudinal axis by at least 45°.

12. The device of claim 1, wherein the arm elements are spaced from one another at an angle around the longitudinal axis by at least 90°.

13. The device of claim 1, wherein each arm element of the at least two arm elements comprises a third arm section which is arranged between the first arm section and the second arm section.

14. The device of claim 13, wherein the third arm section extends at least substantially parallel to the longitudinal axis.

15. The device of claim 1, the tensioning element comprising two tensioning levers connected to a hinge, each tensioning lever comprising a pressure region configured to hold the joint member and to press it against the holding section when the tensioning levers are pressed together.

16. The device of claim 15, wherein the tensioning levers are connected to a tensioning screw configured to press the tensioning levers together.

17. The device of claim 6, wherein the tensioning ring has an annular base element and at least two extensions which are displaceable relative to the base element towards the longitudinal axis and wherein the tensioning ring is held at the extensions.

18. The device of claim 1, wherein an elastic holding element is inserted into the holding section and is configured to receive a first instrument of the medical instruments along the longitudinal axis.

19. The device of claim 1, the holding section being configured to guide a first instrument of the medical instruments and the bearing surfaces being configured to hold a second instrument of the medical instruments.

20. The device of claim 1, the holding section being configured to guide a trocar and the bearing surfaces being configured to hold an endoscope inserted into the trocar.

21. System comprising a device of claim 1, a trocar and an endoscope, wherein the trocar is held by the holding section along the longitudinal axis and the endoscope is inserted into the trocar and is held by the tensioning ring along the longitudinal axis.

* * * * *